United States Patent
Rostock et al.

[11] Patent Number: 5,852,053
[45] Date of Patent: Dec. 22, 1998

[54] USE OF 2-4-AMINO-4-(4-FLUOROBENZYLAMINO) (-1-ETHOXY-CARBONYLAMINOBENZENE FOR THE PROPHYLAXIS AND TREATMENT OF THE NEURODEGENERATIVE DISORDERS

[75] Inventors: Angelika Rostock, Dresden; Chris Rundfeldt, Coswig; Christine Tober, Weinbohla; Reni Bartsch, Dresden, all of Germany

[73] Assignee: Asta Medica Aktiengesellschaft, Dresden, Germany

[21] Appl. No.: 736,166

[22] Filed: Oct. 28, 1996

[30] Foreign Application Priority Data

Oct. 26, 1995 [DE] Germany .................. 195 39 861.0

[51] Int. Cl.$^6$ .................................... A61K 31/27
[52] U.S. Cl. ............................ 514/485; 514/903
[58] Field of Search ...................... 514/485, 903

[56] References Cited

U.S. PATENT DOCUMENTS 5,384,330   1/1995   Dieter et al. ......................... 514/535

*Primary Examiner*—Kimberly Jordan
*Attorney, Agent, or Firm*—Cushman Darby&Cushman IP Group of Pillsbury Madison & Sutro LLP

[57] ABSTRACT

The use of the compound I

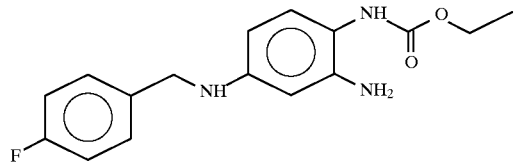

or its pharmaceutically utilizable salts for the propylaxis and treatment of the squelae of chronic reduced cerebral blood supply, in particular of stroke, and for the treatment of nuerodegenerative disorders is claimed.

14 Claims, No Drawings

USE OF 2-4-AMINO-4-(4-FLUOROBENZYLAMINO) (-1-ETHOXY-CARBONYLAMINOBENZENE FOR THE PROPHYLAXIS AND TREATMENT OF THE NEURODEGENERATIVE DISORDERS

This application is based on application no. 19539861.0 filed in Germany on Oct. 26, 1995, the content of which is incorporated hereinto by reference.

BACKGROUND OF THE INVENTION

1. Field of the Invention

The invention relates to the use of 4-amino-4-(4- fluorobenzylamino)-1-ethoxycarbonylaminobenzene of the formula I (designated "compound I")

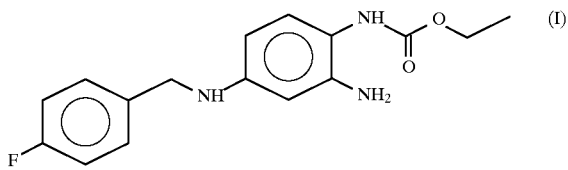

or its pharmaceutically utilizable salts for the production of medicaments for the prophylaxis and treatment of the sequelae of acute and chronic reduced cerebral blood supply and neurodegenerative disorders.

2. Background Information

Compound I is under development as an anticonvulsive agent. It has a broad spectrum of action against various experimentally produced convulsions and in genetic animal models. The activity in animals is higher than that of many anticonvulsive agents introduced. Muscle-relaxant, antipyretic and analgesic actions have furthermore been described (DE 42 00 259).

A problem with many anticonvulsive agents introduced, especially the GABA-increasing substances such as phenobarbital, diazepam and clonazepam but also phenytoin, a blocker of the sodium channel, is the adverse effect on mental powers. By increasing the inhibition in the brain, in addition to the anticonvulsive action a central sedation also occurs, both of which reduce the power of absorption of the patients.

These anticonvulsive agents moreover have neuroprotective activity neither in animal experiments nor in patients. The consequences of a reduced cerebral blood supply, as occurs, for example, in stroke, are not diminished.

In epileptic attacks, an undersupply of the affected areas of the brain also occurs which, however, is attributed not to a reduced blood supply, but to the strong cell activation, as a result of which the reserves are stressed and the supply is no longer adequate.

An anticonvulsive agent which displays a neuroprotective action in the stressed brain is therefore desirable.

A neuroprotective action is also necessary for the therapy of other neurodegenerative disorders. To be counted among these are, for example, Alzheimer's disease, Huntington's chorea, multiple sclerosis, AIDS-induced encephalopathy and other infection-related encephalopathies such as rubella viruses, herpes viruses, borrelia and unknown pathogens, Creutzfeld-Jakob disease, amyotrophic lateral sclerosis (ALS), Parkinson's disease, trauma-induced neurodegenerations and neuronal hyperexcitation states, such as in medicament withdrawal, or by intoxication, and neurodegenerative disorders of the peripheral nervous system such as polyneuropathies and polyneuritides.

Several strategies are at present followed for the treatment of reduced cerebral blood supply and of stroke.

Prophylactically, medicaments can be used which inhibit thrombus formation and increase the flow properties of the blood, such as acetylsalicylic acid. Such a treatment, however, only has a purely prophylactic action; therapy is thus not possible.

If there is a chronic reduced cerebral blood supply, medicaments are used which have vasodilatory activity, such as calcium antagonists.

For the therapy of stroke as acute reduced blood supply, preparations can also be employed which have thrombolytical activity in order to eliminate a possible vascular occlusion. However, these can only be employed if in detailed investigations it has been clearly elucidated that the stroke is not caused by cerebral haemorrhage. In clinical testing for the therapy of stroke, preparations having NMDA-antagonistic action are found which directly inhibit the overactivation of the undersupplied cells. These substances, however, have a high side effect potential. According to the present point of view, they can therefore only be employed with intensive medical care after clear diagnosis. Moreover, NMDA antagonists, due to the inhibition of the plasticity of the brain, have a negative effect on learning power. Prophylactic use of these preparations therefore appears to be excluded from the present point of view, despite the good prophylactic action in animal experiments.

SUMMARY OF THE INVENTION

It is the object of the present invention to make available a medicament having good neuroprotective properties and a low side effect potential for the prophylaxis and treatment of stroke, of reduced cerebral blood supply and of other nerve cell-stressing conditions.

Surprisingly, it has now been found that the compound I has important neuroprotective actions in animal experiments.

Thus, completely new possibilities are opened up for the prophylaxis and treatment of the sequelae of acute and chronic reduced cerebral blood supply, in particular of stroke, and for neurodegenerative disorders.

DETAILED DESCRIPTION OF THE INVENTION

Pharmacological investigations:

The aim of the investigation with compound I in models of learning power and neuroprotection was to estimate the possible effects of these parameters, since compound I, inter alia, displays a GABA-ergic action. Since the epilepsy patient as a result of the repeated attacks often already suffers from a learning power deficit, these experiments were carried out on animals which had been exposed to an amnesic factor and whose learning power was thus reduced. To do this, the animals were either repeatedly treated with electroshock or exposed to alcohol withdrawal; to estimate the direct neuroprotective action, a chronic reduced blood supply to the brain was produced by tying off afferent blood vessels. All this damage leads to a reduction in the learning power, which is to be assessed as an indicator of nerve cell damage. GABA-increasing antiepileptically active medicaments such as diazepam and sodium channel blockers such as phenytoin do not have any positive effects in these models and in higher doses adverse effects on the learning power can even occur.

Investigation models:

Learning power damage due to reduction of the blood supply to the brain

In this model, one of the carotid arteries of rats is tied off under anaesthesia.

The animals wake from the anaesthesia and then have a decreased learning power. This was determined by means of the rod jumping test. In this test, the animals must learn to escape a slight electric shock to the foot, which is announced to them beforehand by an acoustic signal, by jumping onto a vertical rod suspended above the floor.

The learning power of the animals is measured in percent as the number of reactions caused (jumping onto the rod during the acoustic signal phase).

Untreated and sham-operated animals (anaesthetized and vessels exposed, but no ligature performed) learn the combination of acoustic signal and the following unpleasant shock to the foot very rapidly. After 4 test days with 10 exposures daily, the animals react almost with each sound signal with a jump onto the vertical rod.

As a result of the ligature of the left carotid, this learning power is reduced to approximately half. Animals pretreated with 2 mg/kg i.p. of compound I an hour before each test phase unexpectedly learnt just as well, despite existing injury due to the ligature, with a tendency to be even better than non-operated animals. However, if the animals were pretreated with diazepam (0.3 mg/kg i.p., 1 hour before each training phase), then the learning power remained just as poor as in the untreated injured animals.

The same applies to treatment with the anticonvulsive agent phenytoin (3 and 10 mg/kg); it was not possible to improve the learning power.

An improvement in the learning power despite the existing reduced blood supply is to be regarded as an indicator of a cytoprotective action, as only fully functional nerve cells are capable of learning.

It is therefore to be expected that compound I manifests a cytoprotective action, for example in the peripheral region of an infarct, where a reduced blood supply is also present or on stressed cells which are subject to a relative energy deficiency. As a result, the infarct volume and thus the damage should remain lower and survival should be made possible for severely stressed cells.

Significant differences between the sham-operated control group and the control group with a ligature (t test) are marked by $^+p<0.05$ and $^{++}p<0.01$.

Significant differences between the control group with a ligature and the treated group are marked by $* p<0.05$ and $** p<0.01$.

Compound I not only exhibited an excellent action in this model, it was also possible to reduce the decrease in learning power produced by repeated application of electroshock by pretreatment with 2 mg/kg of the compound I an hour before the test.

While on the 4th test day injured test animals only showed $32\pm2.9\%$ of reactions caused, the treated animals were able to carry out $45\pm4.5\%$ of reactions caused correctly. This action was also detectable after a pretreatment time of 2 hours. The number of reactions caused rose here from $35\pm3.7\%$ in the control group to $52\pm3.9\%$ in the treated group.

It was also possible to positively affect the decrease in learning power due to alcohol withdrawal.

Compound I can thus be employed as a highly specific active compound for the treatment of the sequelae of acute and chronic reduced cerebral blood supply, in particular of stroke, and in all conditions during and after stressing of nerve cells.

On account of the low side effects of the substance in animal experiments, compound I can also be employed for the prophylaxis of the abovementioned disorders and conditions.

Compound I is structurally related to flupirtin, a clinically introduced central analgesic agent. While in the case of flupirtin an NMDA-antagonistic action was found (WO 95/05175), it was possible to exclude such an action for compound I through in vitro experiments. Neither an affinity for the various binding sites of the NMDA receptor nor a direct effect on the flow induced by NMDA was found.

In more involved investigations on the central analgesic action of the compound I in the hot plate test, in contrast to

TABLE 1

Number of reactions indicated in % in the rod jump test after injury as a result of ligature of the left carotid.

| Left carotid ligature | 1st day | 2nd day | 3rd day | 4th day |
| --- | --- | --- | --- | --- |
| Compound I 2 mg/kg | $20 \pm 2.6$ | $59 \pm 7.7 *$ | $64 \pm 9.1 *$ | $70 \pm 6.5 **$ |
| Control ligature | $16 \pm 2.2$ | $30 \pm 3.7++$ | $36 \pm 3.1++$ | $39 \pm 3.8++$ |
| Control sham ligature | $18 \pm 2.0$ | $55 \pm 6.9$ | $59 \pm 5.9$ | $62 \pm 5.9$ |
| Diazepam 0.3 mg/kg | $9 \pm 1.8$ | $37 \pm 4.2 *$ | $38 \pm 5.1$ | $44 \pm 5.0$ |
| Control ligature | $13 \pm 3.0 +$ | $30 \pm 2.1 ++$ | $37 \pm 2.6 ++$ | $38 \pm 3.6 ++$ |
| Control sham ligature | $21 \pm 2.3$ | $52 \pm 5.1$ | $64 \pm 4.8$ | $71 \pm 3.8$ |
| Phenytoin 10 mg/kg | $13 \pm 2.1$ | $38 \pm 4.2$ | $45 \pm 5.6$ | $48 \pm 4.4$ |
| Pheytoin 3 mg/kg | $14 \pm 1.6$ | $38 \pm 3.6$ | $39 \pm 4.1$ | $42 \pm 4.7$ |
| Control ligature | $13 \pm 3.0 +$ | $30 \pm 2.1 ++$ | $37 \pm 2.6 ++$ | $38 \pm 3.6 ++$ |
| Control sham ligature | $21 \pm 2.3$ | $52 \pm 5.1$ | $64 \pm 4.8$ | $71 \pm 3.8$ | flupirtin it was possible to exclude a central analgesic action, as has been detected in the hot plate test on mice for flupirtin with an average effective dose of 30 mg/kg.

NMDA antagonists can cause severe psychotic disorders, such as ataxia with stereotypic symptoms.

Compound I and processes for its preparation are known (DE 42 00 259).

The compound can be converted in a known manner into the customary formulations such as tablets, capsules, coated tablets, pills, granules, syrups, emulsions, suspensions and solutions, using inert, non-toxic, pharmaceutically suitable excipients and/or auxiliaries.

The daily dose of the compound I in the case of oral or parenteral administration should be 50–500 mg. If necessary, it is possible to deviate from the amounts mentioned, namely depending on the body weight and the specific type of administration route.

What is claimed is:

1. A method for the treatment of a neurodegenerative disorder, said method comprising administering to an individual an effective amount of a compound of formula I

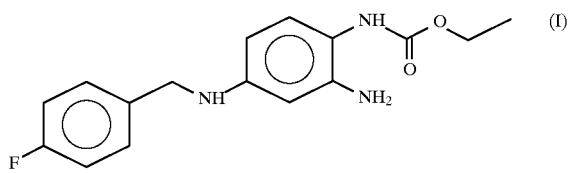

or a pharmaceutically utilizable salt thereof.

2. The method of claim 1 wherein said neurodegenerative disorder is Alzheimer's disease.

3. The method of claim 1 wherein said neurodegenerative disorder is Huntington's chorea.

4. The method of claim 1 wherein said neurodegenerative disorder is multiple sclerosis.

5. The method of claim 1 wherein said nuerodegenerative disorder is amyotrophic lateral sclerosis.

6. The method of claim 1 wherein said neurodegenerative disorder is an infection-related encephalopathy.

7. The method of claim 6 wherein said infection-related encephalopathy is caused by an infection selected from the group consisting of AIDS, rubella viruses, herpes viruses, and borrelia.

8. The method of claim 1 wherein said neurodegenerative disorder is Creutzfeld-Jakob disease.

9. The method of claim 1 wherein said neurodegenerative disorder is Parkinson's disease.

10. The method of claim 1 wherein said neurodegenerative disorder is a trauma-induced neurodegeneration or neuronal hyperexcitation state.

11. The method of claim 10 wherein said neurodegenerative disorder is caused by withdrawal from intoxication.

12. The method of claim 1 wherein said neurodegenerative disorder is a disorder of the peripheral nervous system.

13. The method of claim 12 wherein said disorder is a polyneuropathy or polyneuritide.

14. The method of claim 1, wherein said compound is administered in a dosage of 50–500 mg per day.

* * * * *

UNITED STATES PATENT AND TRADEMARK OFFICE
CERTIFICATE OF CORRECTION

PATENT NO. : 5,852,053
DATED : December 22, 1998
INVENTOR(S) : ROSTOCK, et al.

It is certified that error appears in the above-identified patent and that said Letters Patent is hereby corrected as shown below:

On the title page, item [54]: & Col. 1 line 1,:

In the title, line 1, change " 2-4-AMINO-4-(4- " to -- 2-AMINO-4-(4- --.

In column 1, line 1, change " 2-4-AMINO-4-(4- " to -- 2-AMINO-4-(4- --.

In column 1, line 12, change " 4-amino-4-(4- " to to -- 2-amino-4-(4- --.

Signed and Sealed this

Twenty-second Day of June, 1999

Attest:

Q. TODD DICKINSON

*Attesting Officer*    Acting Commissioner of Patents and Trademarks